United States Patent [19]

Rehner et al.

[11] Patent Number: 4,931,392
[45] Date of Patent: Jun. 5, 1990

[54] PROCESS FOR STABILIZING KINASE

[75] Inventors: Helmut Rehner, Weilheim; Knut Bartl, Wilzhofen; Peter Stegmüller, Augsburg; Wilhelm Tischer, Peissenberg; Sibylle Rollinger, Weilheim, all of Fed. Rep. of Germany

[73] Assignee: Boehringer Mannheim GmbH, Mannheim, Fed. Rep. of Germany

[21] Appl. No.: 355,039

[22] Filed: May 15, 1989

Related U.S. Application Data

[63] Continuation of Ser. No. 924,698, Oct. 29, 1986, abandoned.

[30] Foreign Application Priority Data

Nov. 12, 1985 [DE] Fed. Rep. of Germany ....... 3540076

[51] Int. Cl.$^5$ ........................... C12N 9/12; C12Q 1/50
[52] U.S. Cl. .................................... 435/188; 435/183; 435/194; 435/226
[58] Field of Search ............... 435/186, 184, 188, 178, 435/17, 194

[56] References Cited

U.S. PATENT DOCUMENTS 3,876,501  4/1975  Hanushewsky ...................... 195/68

FOREIGN PATENT DOCUMENTS 0045122  3/1982  European Pat. Off. .
0049475  4/1982  European Pat. Off. .

OTHER PUBLICATIONS

Gerhardt et al., Clinical Chemistry, vol. 28, No. 4, 1982, pp. 719–720.
Russian Chemical Reviews, Uspekhi Knimii, May 1980, pp. 385–403, 4402 Chem. Abstr. Biochemistry Sections, vol. 93, 1980.

*Primary Examiner*—Thomas G. Wiseman
*Assistant Examiner*—Patricia Carson
*Attorney, Agent, or Firm*—Felfe & Lynch

[57] ABSTRACT

The present invention provides a process for stabilizing creatine kinase by disulphide modification, wherein creatine kinase is reacted in any desired sequence
(a) with a molar excess of disulphide and/or thiosulphonate and
(b) with a molar excess of water-soluble carbohydrate as carrier.

14 Claims, 5 Drawing Sheets

PROCESS FOR STABILIZING KINASE

This application is a continuation of application Ser. No. 924,698, filed Oct. 29, 1986 now abandoned.

The present invention is concerned with a process for stabilising creatine kinase in solution by disulphide modification, as well as with a process for using this stabilised creatine kinase.

The determination of creatine kinase plays an important part in clinical-chemical analysis. For the control of such analyses and for calibrating automatic analysers for the determination of creatine kinase activity, it is necessary to have available control and calibration sera with a known content of creatine kinase activity. A prerequisite for this is that the components in the control or calibration serum are stable over a predetermined period of time and that the creatine kinase activity does not change substantially during this period of time. Furthermore, it is important that the creatine kinase present in the control or calibration serum behaves in the same way as the creatine kinase present in the sample material from a patient.

Control and calibration sera (comprehensive sera) are usually made up on the basis of human serum, animal serum or bovine serum albumin. The creatine kinase content must be increased by the addition of exogenic creatine kinase activity in order to ensure a good measurability and precision and an optimum calibration of the apparatus.

It has long been known that this exogenic creatine kinase activity in control sera is unstable. Therefore, attempts have not been lacking to stabilise the creatine kinase activity in control sera. Because of the inherent instability of enzymes, it is usual to lyophilise control and calibration sera which contain enzymes in order to improve the storage stability. For use, the lyophilised control and calibration sera are reconstituted. In general, these reconstituted solutions obtained from lyophilisates have only a relatively short stability which, depending upon the parameters, can be from about 24 hours to about 5 days. In most cases, it is necessary to store in a refrigerator. Furthermore, the use thereof is further limited when, as is generally the case, several parameters are to be monitored or calibrated in automatic analysers simultaneously or over short intervals of time. In this case, the time period in which the control or calibration sera can be used is determined by the parameters which have the shortest period of stability.

The long-term stability in a liquid medium with refrigerator storage, i.e. at a temperature of from 2° to 8° C., should be at least one year. However, hitherto this problem could not be solved and there is, therefore, a need for a control or calibration serum which is present in liquid form, can be used immediately and, even after opening the container, can be stored in a refrigerator for a comparatively long time, i.e. for several weeks.

Therefore, attempts have not been lacking to prolong the period of use of reconstituted control and calibration sera and so to improve the storage stability of the control or calibration sera parameters that a lyophilisation is no longer necessary.

Thus, inter alia, the attempt has been made to protect creatine kinase against oxidation and thus against loss of activity by the addition of thiol compounds. However, a disadvantage of thiol compounds is that, in a serum which contains these thiol compounds, several parameters cannot be determined simultaneously since the thiol compounds disturb analytical methods of determination because, being reducing agents, they influence, for example, colour reactions for the determination of hydrogen peroxide.

Furthermore, it is known from European Patent Specification No. 0045122, for the improvement of the creatine kinase stability in control and calibration sera, reversibly to modify the reversible modification of the reactive SH groups of the enzyme by appropriate modification reagents, for example disulphides, by means of disulphide exchange according to the following equation:

In this way, the reactive SH groups of the enzyme are protected against oxidation and other serum inhibitors.

Another possibility is disclosed in Federal Republic of Germany Patent Specification No. 28 56 988 according to which a lyophilised control or calibration serum is reconstituted with an aqueous solution of about 20 to 40% ethylene glycol or a homologue thereof. The ethylene glycol lowers the freeze point of the control and calibration serum matrix to such an extent that the product can be stored in liquid form at −20° C. without freezing. In this form, the enzymes and the other parameters in the products are stable for several months. After removal from the refrigerator, the product can, after warming up, be used immediately. Since ethylene glycol is an excellent bacteriostatic, the control and calibration serum is also stable for several weeks when kept in a refrigerator. A product which is made up by this process is commercially available under the name "Decision Control". However, this process suffers from a decisive disadvantage. Due to the large content of ethylene glycol, the product does not behave like a patient's serum. The high viscosity of the ethylene glycol changes the pipetting behaviour of the control and calibration serum so that analytical errors can occur. Furthermore, various analytical detection processes are disturbed by the addition of ethylene glycol. Thus, this product also still has some disadvantages so that it cannot be generally used as control or calibration serum.

Another suggestion, given in "Advances in Biochemical Engineering", pub. Springer Verlag, Vol. 12, pp. 83–90/1979, is to stabilise enzymes by binding to carbohydrates. However, this stabilisation is insufficient.

Furthermore, it is known from European Patent Specification No. 0049475 covalently to bind enzymes to polymers for stabilisation, the polymers containing anhydrides as functional units. It is a disadvantage of this process that, after the stabilisation reaction, only about 5 to 10% of the original activity of the enzyme is maintained.

It is an object of the present invention to provide a process with which creatine kinase can be stabilised to such an extent that it can be stored at refrigerator temperature for at least a year without loss of activity and that, even after opening the container, can be kept for a comparatively long time without having to be lyophilised for stabilisation. Furthermore, the stabilised creatine kinase is to be present in liquid form and to be immediately usable. In addition, it is an object of the present invention so to stabilise the creatine kinase that the stabilisation does not substantially decrease the activity.

Thus, according to the present invention, there is provided a process for stabilising creatine kinase by disulphide modification, wherein the creatine kinase is reacted in any desired sequence (a) with a molar excess of disulphide and/or thiosulphonate and
(b) with a molar excess of water-soluble carbohydrate.

Surprisingly, we have found that the creatine kinase in control and calibration sera can be so stabilised by two stabilising steps, namely, by the protection of the SH groups by means of disulphide exchange and enzyme stabilisation by fixing on to a water-soluble carbohydrate, that the enzyme in the control or calibration serum is storage-stable in liquid form at 4° to 8° C. for a comparatively long period of time without any noteworthy decrease of activity. An important advantage of the process according to the present invention is that the creatine kinase can be stabilised in solution without any additives. In this way, the disadvantages of the known methods are overcome.

The process according to the present invention for stabilising creatine kinase consist of the following steps used in any desired sequence:

(a) creatine kinase isolated from human and animal tissue is reacted with an excess of disulphide or thiosulphonate. The free SH groups of the creatine kinase thereby react with the disulphide or thiosulphonate with the formation of mixed disulphides. These protective groups can then, when the control or calibration serum in question is to be used, again be split off easily by the addition of known agents so that the activity of the enzyme is then again available.

(b) The creatine kinase is reacted with an excess of water-soluble carbohydrate. The carbohydrate is preferably activated in known manner and this activated carbohydrate is then covalently bound to the creatine kinase.

The sequence of the two steps (a) and (b) is as desired. However, it is preferred first to protect the SH groups by reaction with disulphide or thiosulphonate and subsequently to react the so-obtained creatine kinase disulphide with the activated carbohydrate.

Creatine kinase preparations from various animal species can be used for the process according to the present invention. Thus, the creatine kinase can be obtained from rabbit muscle, pig muscle, pig heart, rhesus monkey skeletal muscle, chicken muscle, bovine heart and other sources. In carrying out the process according to the present invention, it is preferred, however, to use creatine kinase from rabbit or chicken muscle or from pig or bovine heart.

In carrying out step (a) of the process according to the present invention, the creatine kinase is reacted with a disulphide or thiosulphonate. As disulphide, it is preferred to use cystine, homocystine or a cystine derivative, a penicillinamine disulphide and/or bis-(2-pyridyl-N-oxide) disulphide. As cystine derivatives, there are preferably used cystine methyl ester and cystamine. The disulphide component can be used in a molar ratio of enzyme to disulphide of from 1:5 to 1:20, referred to the SH groups.

There can also be used the reaction with a thiosulphonate. As thiosulphonate, there is thereby preferably used methanethiosulphonic acid S-methyl ester. The thiosulphonate can be used in a molar ratio of enzyme to thiosulphonate of from 1:0.5 to 1:5, referred to the SH groups.

In the case of the reaction of the creatine kinase with the disulphide or thiosulphonate, the enzyme is preferably pesent in a concentration of 0.01 to 1 mmole/liter, an enzyme concentration of from 0.05 to 0.5 mmole/liter being especially preferred.

In step (b) of the process according to the present invention, the creatine kinase or the creatine kinase disulphide is covalently bound to a water-soluble carbohydrate.

A preferred carbohydrate is dextran. However, very good results are also achieved with other water-soluble carbohydrates, especially with soluble starch. High molecular weight polymers of mono- and disaccharides such as are obtained, for example, by reaction with epihalohydrins, for example "Ficoll", also prove to be well suited.

In the most preferred embodiment, the creatine kinase or the creatine kinase disulphide is covalently bound to be water-soluble dextran with a molecular weight of from 4000 to 500,000.

In the case of the reaction of the creatine kinase with the carrier, the carbohydrate used as carrier is present dissolved in water, the concentration of the carrier in the aqueous solution preferably being in the range of from 1 to 10%.

The carbohydrate is activated in known manner, activation preferably taking place by reaction of the carbohydrate with trichlorotriazine (TCT), cyanogen bromide or 1-cyano-4-dimethylaminopyridinium (CDAP) tetrafluoroborate. The ratio of activation agent to carbohydrate is preferably in the range of from 1:5 to 1:10, referred to the weight of the two components. The activated carbohydrate is then reacted with the creatine kinase. It is thereby preferred to use a ratio of enzyme to carbohydrate of from 1:10 to 1:30, referred to the weight.

The creatine kinase derivative obtained after carrying out both steps can be kept in this form in solution without any stabilising additives for a comparatively long time, i.e. at least a year at 4° to 8° C., i.e. in a refrigerator, without the activity of the enzyme changing substantially.

In order further to improve the stability of the creatine kinase, the SH groups of which are protected by disulphide exchange, bound to a soluble carbohydrate, in an especially preferred embodiment, the enzyme-containing solution is placed into containers and subsequently covered with an inert protective gas. As inert protective gas, it is preferred to use nitrogen. If a constant carbonate/bicarbonate nominal value is desired, it is preferred to use a mixture of nitrogen and carbon dioxide as protective gas.

The creatine kinase derivative stabilised according to the present invention can be used for the preparation of a control or calibration serum. For the determination of the creatine kinase activity, the disulphide bridges, which have been introduced to protect the SH groups of the enzyme, must be split again. This takes place in known manner by the addition of a thiol compound. In the case of the known processes for the determination of the creatine kinase activity, a thiol compound is generally added which serves for the reactivation of the creatine kinase enzyme present in the sample in oxidised or inhibited form. This thiol compound contained in the reagent suffices in order completely to convert the stable creatine kinase derivative obtained according to the present invention into an active preparation in the time provided for carrying out the test. As thiol compound, it is preferred to use N-acetylcysteine.

In the preparation of the control or calibration serum, for the determination of the creatine kinase, an appropriate matrix is chosen. Control and calibration sera are usually made up on the basis of human serum, animal serum or pure protein solutions. To this matrix is then added the stabilised creatine kinase derivative prepared according to the present invention in the activity appropriate for the intended purpose. Furthermore, for the preparation of control sera, there can be added conventional additives, such as preserving agents and/or antibiotics. The control or calibration serum can then be stored in this form at 4° to 8° C. However, it is also possible to lyophilise the control or calibration serum and then, for use, to reconstitute it with water.

If, as matrix for the preparation of the control or calibration serum, there is used human serum or animal serum, it is preferred to inactivate by appropriate measures the enzyme activities endogenically present in the serum. Especially preferably, the residual activity in the serum is so reduced that it amounts to less than 3% of the subsequently desired activity in the control or calibration serum.

For the preparation of a control or calibration serum, it is especially preferred to use a pure protein solution, the composition of which can be adjusted according to the intended purpose of use of the control or calibration material. For the preparation of a universally usable control serum, which can be used as standard for many different determinations, all important enzymes, substrates and metabolites are added to the protein solution. Lipids are supplemented by the addition of appropriate lipid fractions.

If the control or calibration serum is to be stored in a liquid state for a comparatively long period of time, it is especially preferred sufficiently to preserve the serum again attack by micro-organisms. For this purpose, the solutions are preferably filtered free of micro-organisms before filling into bottles or are at least filtered so that they have a low content of micro-organisms, membrane filters being used with a pore size of $\leq 0.2$ $\mu$m. A preserving agent is then added to the serum. The addition of sodium azide is especially preferred. Additions of antibiotics, such as chloramphenicol, gentamycin and/or penicillin, are also appropriate for the preservation of the sera.

The present invention also provides a control or calibration serum for the determination of creatine kinase, which is characterised in that it contains the creatine kinase in the form of its reaction product with a disulphide or thiosulphonate and bound to a water-soluble carbohydrate.

The control or calibration serum preferably contains a creatine kinase with an activity of 50 to 1000 U/ml. (25° C.), a creatine kinase with an activity of from 150 to 600 U/ml. being especially preferably used.

The creatine kinase stabilised according to the present invention is characterised in that the enzyme creatine kinase is present in the form of a reaction product with a disulphide or thiosulphonate and bound to a water-soluble carbohydrate. This creatine kinase according to the present invention is especially suitable for the preparation of control and calibration sera for the determination of creatine kinase.

The control or calibration sera prepared according to the present invention with the stabilised, soluble creatine kinase derivative are stable for at least a year when stored at 4° to 8° C. They can be stored not only in liquid form at refrigerator temperature but also in lyophilised form. The lyophilised control or calibration sera, after reconstitution with water or an appropriate diluent, are also stable for a comparatively long period of time.

The following Examples are given for the purpose of illustrating the present invention. The creatine kinase derivatives obtained according to the present invention were assessed by thermal stressing experiments. For this purpose, the liquid control or calibration sera samples are well closed and stored at 35° C., the activity being measured after storage at 35° C. for 1, 2, 3 and 6 weeks and compared with the creatine kinase activity at the commencement of the stressing. It was shown that the enzyme activity of the creatine kinase derivatives in control and calibration sera remained stable for storage at refrigerator temperature for at least a year when the recovery of the enzyme activity of the samples stored at 35° C. amounted to at least 90% after 3 weeks.

EXAMPLE 1

(A) Preparation of a Stable Creatine Kinase Derivative 164 mg. of rabbit muscle creatine kinase are dissolved in 20 ml. of carbonate buffer (10 mM, pH 8.0) which contains 2 mmole cystine per liter, and left to stand for 1 hour at ambient temperature. There follows a dialysis against carbonate buffer (10 mM, pH 8.0).

6 g. dextran T40 are dissolved in 40 ml. water and cooled in an ice-bath to ±0° C. 600 mg. 2,4,6-trichloro-1,3,5-triazine are then dissolved in 10 ml. deep-cooled dimethylformamide and added to the batch. The pH value is adjusted to 5.0 by addition of 0.5N aqueous sodium hydroxide solution and kept at this value. After termination of the reaction, i.e. when no further change of the pH value takes place, the activated dextran is purified by reprecipitating three times with, in each case, a twofold by volume excess of deep-cooled acetone. The acetone precipitate is, in each case, dissolved with iced water.

An aliquot of the creatine kinase solution (about 8.6 mg. of protein per ml.) is mixed with the same volume of the dextran solution activated with the trichlorotriazine (17.2 mg./ml.). The solution is left to stand for 24 hours at ambient temperature. Thereafter, 10% by volume of glycine buffer (1M, pH 8.0) are added thereto and the solution again left to stand overnight.

For the purposes of comparison, a freshly prepared rabbit muscle creatine kinase solution, the SH groups of which had not been protected, was bound, as described above, directly to activated dextran T40. Here, too, the protein to dextran ratio is 1:2.

The yields of again reactivatable creatine kinase activity are as follows: after SH protection after reaction with cystine 92% and after SH protection by means of cystine and fixing to dextran T40 64%.

(B) Preparation of a Control and Calibration Serum

The matrix for the control serum is a 6% bovine serum albumin solution. For the preparation of a universal control or calibration serum (calibrator), all essential enzymes (e.g. α-Amylase, AP, ASAT, ALAT, γ-GT, LDH, HBDH, Lipase), substrates (lipids lipidfractions), metabolites, (e.g. albumine, creatinine, glucose, urea, uric acid, cholesterol) and electrolytes (e.g. Na, K, Ca, Li, Fe, Mg, Cl, phosphate) are added to this protein solution. Lipids are supplemented by the addition of appropriate lipid fractions. The pH value of the control or calibration serum is adjusted to about 7.0.

In order to ensure a long storage of the control or calibration serum in a liquid state without attack by micro-organisms, the control serum matrix is filtered to a low micro-organism content with the use of a membrane filter with a pore size of 0.2μ and preserved by the addition of 250 mg. sodium azide per liter and 100 mg. gentomycin per liter.

To these control serum matrices are, in each case, added
(a) native rabbit muscle creatine kinase,
(b) rabbit muscle creatine kinase, the SH groups of which are protected with cystine,
(c) rabbit muscle creatine kinase with unprotected SH groups which is covalently bound to dextran T40 activated with trichlorotriazine, and
(d) rabbit muscle creatine kinase, the SH groups of which are protected with cystine and which is covalently bound to dextran T40 activated with trichlorotriazine.

In all sera, the creatine kinase activity is adjusted to about 500 U/liter. These four control or calibration sera are subjected to a thermal stressing for testing the stability. The individual solutions are placed into small flasks in an amount of 5 ml. and well closed in liquid form and stored at 35° C. The creatine kinase activity is measured every week for 5 or 6 weeks and compared with the creatine kinase activity at the beginning of the stressing.

The creatine kinase activity is determined with the optimised standard method according to the recommendation of the Deutsche Gesellschaft für klinische Chemie (see Clin. Chem., 22, 650–662/1976) at 25° C.

Figure 1:
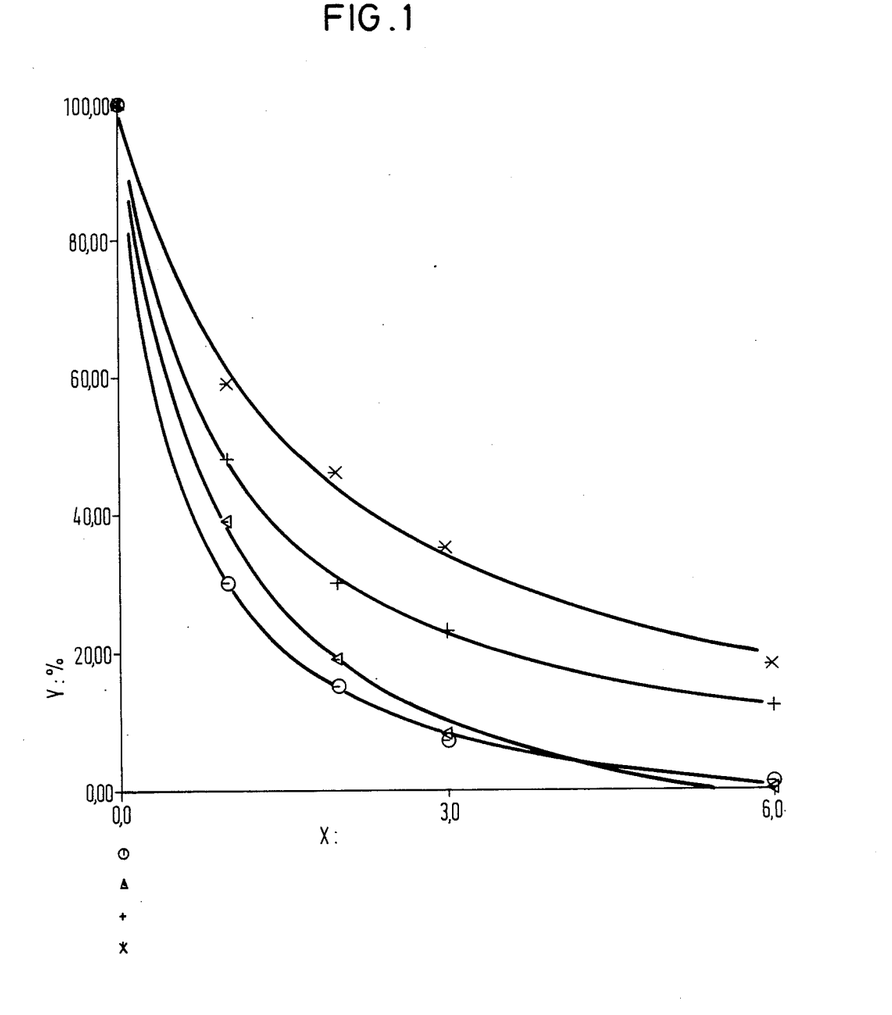

In FIG. 1 of the accompanying drawings, there are summarised the results of the stress testing of the four control sera. In each case, there is given the activity in % after stressing of the four above-described creatine kinase preparations as activity after stressing by starting activity before stressing × 100%.

EXAMPLES 2–6

There is used the procedure described in Example 1. Instead of cystine, for comparison there are used the following disulphides in the same concentration (2 mMole/liter) as in Example 1:
cystamine
cystine methyl ester
homocystine
penicillinamine disulphide and
bis-(2-pyridyl-N-oxide)-disulphide.

After fixing the individual SH-protected creatine kinase preparations to TCT dextran T40 and the use in control or calibration solutions, after stressing for 3 weeks, the following stabilities are measured in comparison with cystine as SH protection component. The results are set out in the following Table 1 and are also given in FIG. 2 of the accompanying drawings.

TABLE 1

| disulphide used | % activity after storage for 3 weeks at 35° C. |
|---|---|
| cystine | 37 |
| cystamine | 27 |
| cystine methyl ester | 23 |
| homocystine | 34 |
| penicillamine disulphide | 30 |
| bis-(2-pyridyl-N-oxide)-disulphide | 30 |

TABLE 1-continued

| disulphide used | % activity after storage for 3 weeks at 35° C. |
|---|---|
| disulphide | |

EXAMPLE 7

Preparation of a stable creatine kinase in which the SH-protection is not achieved by disulphide exchange as in Examples 1 to 6 but by reaction with thiosulphonate.

17 mg. rabbit muscle creatine kinase are dissolved in 2 ml. glycine buffer solution (10 mM, pH 7.8) and reacted with 50 μl. methanethiosulphonic acid S-methyl ester solution (20 mM in 10 mM glycine buffer, pH 7.8) for 30 minutes at 0° C.

There follows a purification with a Sephadex G25 column and a dialysis against 10 mM carbonate buffer (pH 8.0), as well as the fixing of the creatine kinase derivative obtained to TCT-activated dextran T40 as described in Example 1.

The creatine kinase activity after stressing for 3 weeks in a control/calibration serum prepared according to Examples 1 to 6 is 58%.

EXAMPLES 8–11

Creatine kinase preparations from various animal species are used. The SH protection, the fixing to dextran and the preparation of the control or calibration sera is carried out as in Example 1.

The finding again of the initial activity after storage for 3 weeks of the liquid control sera at 35° C. is, in the case of the creatine kinase preparations used, as follows:

TABLE 2

| source of the creatine kinase | % activity after storage for 3 weeks at 35° C. |
|---|---|
| rabbit muscle | 37 |
| pig muscle | 52 |
| pig heart | 57 |
| rhesus monkey skeletal muscle | 49 |
| chicken muscle | 42 |

EXAMPLE 12

Native and SH-protected rabbit muscle creatine kinase are used.

The SH protection takes place, as described in Example 1, by means of reaction with cystine.

The fixing of the enzyme takes place on to dextran T40 activated with cyanogen bromide, there essentially being used the standard process described by Marshall (activation and fixing) (American Chemical Society Symposium Series, 123, 125–140/1980). The ratio of cyanogen bromide to dextran is 1:3 and the protein:dextran ratio is 1:6.

The yields of again reactivatable creatine kinase activity are as follows: 92% of the SH-protected enzyme (after reaction with cystine), 62% of the SH-protected enzyme fixed to dextran and 64% of the native enzyme fixed to dextran.

Analogously to Example 1, to the control serum matrix are added, in each case, about 500 U/liter of:
(a) native rabbit muscle creatine kinase, (b) rabbit muscle creatine kinase after SH protection by means of cystine,
(c) rabbit muscle creatine kinase without SH protection but fixed on to dextran T40 activated with cyanogen bromide and
(d) rabbit muscle creatine kinase with SH protection by means of cystine and fixing on to dextran T40 activated with cyanogen bromide.

Figure 2:
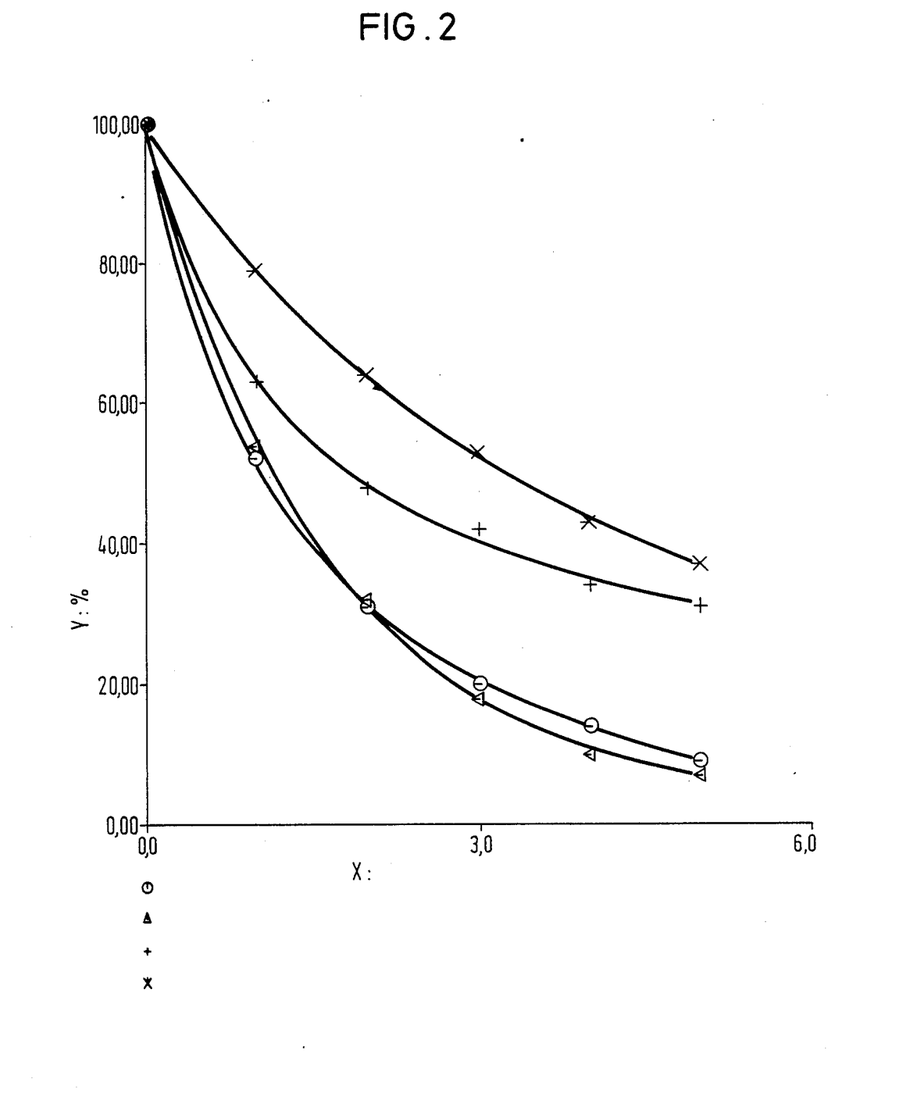

FIG. 2 of the accompanying drawings shows the results of the stress testing.

EXAMPLE 13

Native and SH-protected rabbit muscle creatine kinase are used. The SH protection takes place as described in Example 1 by means of reaction with cystine.

The fixing of the enzyme takes place according to J. J. Marshall (American Chemical Society Symposium Series, 123, 124–140/1980) on to dextran T40 which had been activated with CDAP-BF$_4$ according to the method of J. Kohn and M. Wilchek (Appl. Biochem. Biotech., 9, 285–305/1984).

Analogously to Example 1, to the control serum matrix are added, in each case, about 500 U/liter of:
(a) native rabbit muscle creatine kinase,
(b) rabbit muscle creatine kinase after SH protection by means of cystine,
(c) rabbit muscle creatine kinase without SH protection but fixed on to CDAP-activated dextran T40 and
(d) rabbit muscle creatine kinase with SH protection and fixing to CDAP-activated dextran T40.

Some of the control serum bottles are additionally covered with a protective gas atmosphere of nitrogen.

Figure 3:
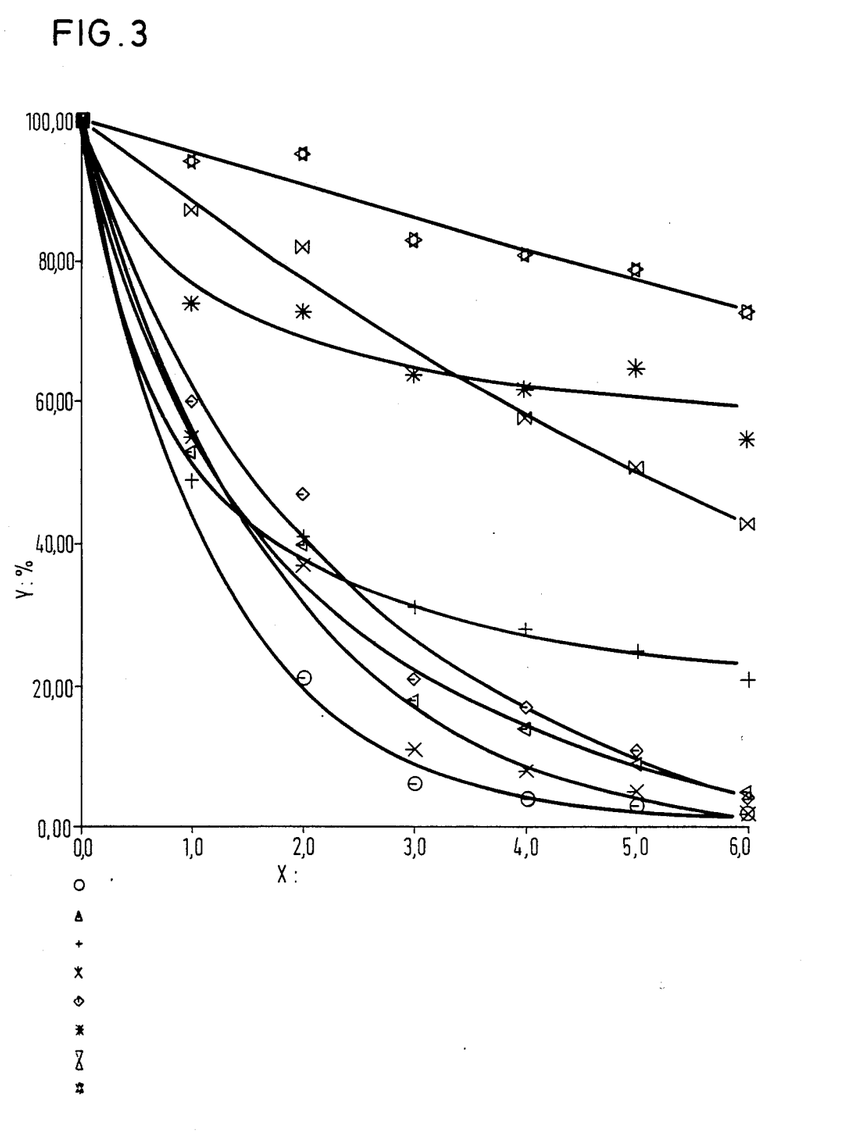
Figure 3A:
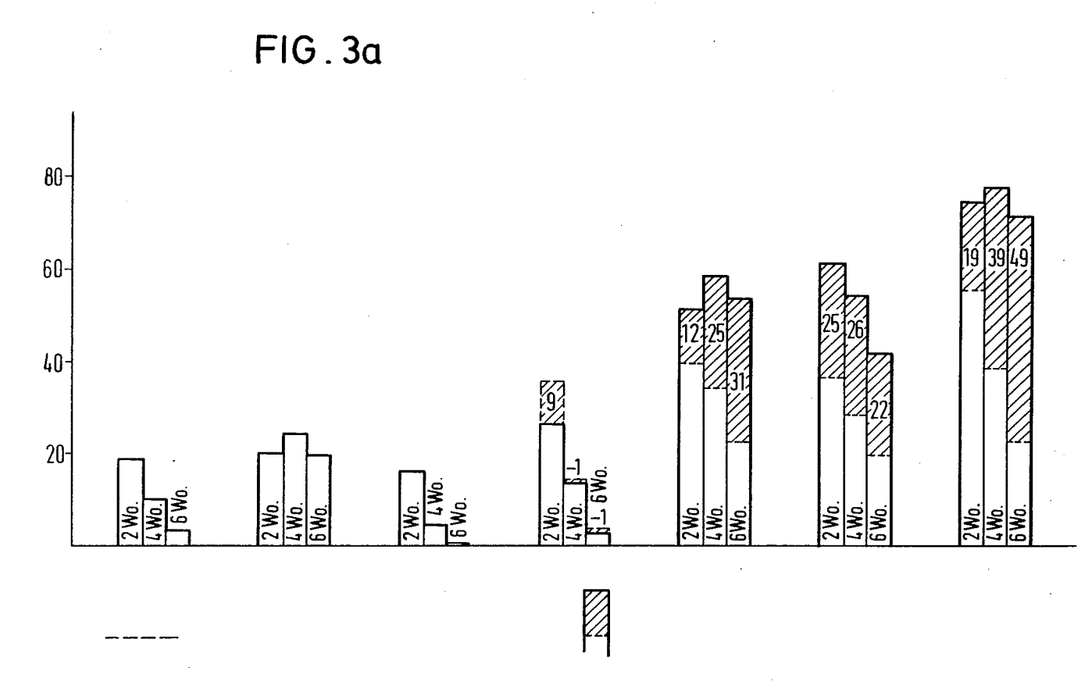

FIGS. 3 and 3a of the accompanying drawings show the results of the stress testing in which the control sera are stored in liquid form at 35° C. as in the other Examples.

EXAMPLE 14

The procedure used in Example 13 is used. Use is made of SH-protected rabbit muscle creatine kinase (SH protection by means of cystine) and the protein:dextran ratio varies from 1:3 to 1:20.

The activity yields of the SH-protected enzyme preparations fixed on to dextran T40 in dependence upon the protein:dextran ratio are summarised in the following Table 3:

TABLE 3

| protein:dextran ratio | activity yield (% of the initial activity) |
| --- | --- |
| 1:3 | 65 |
| 1:6 | 54 |
| 1:10 | 55 |
| 1:20 | 48 |

Figure 4:
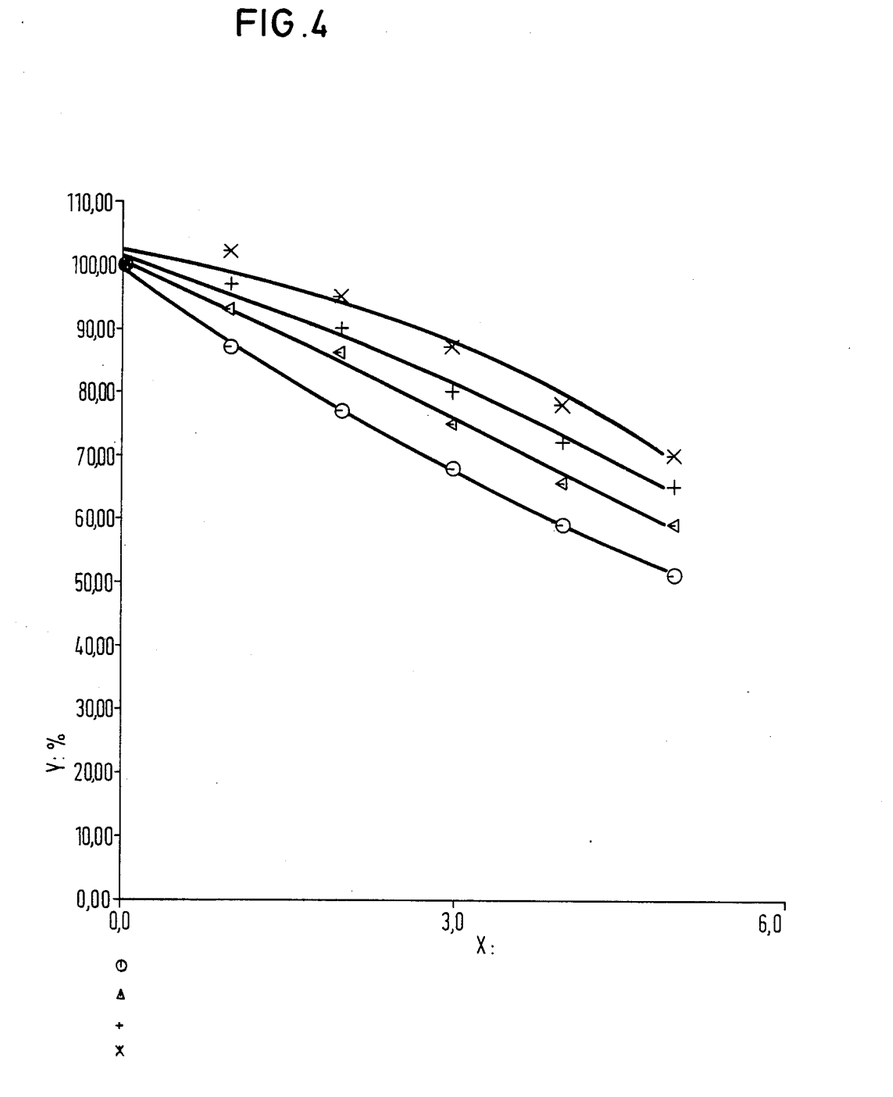

FIG. 4 of the accompanying drawings shows the result of the stress testing. The control sera preparations are stored in liquid form at 35° C. under an atmosphere of air.

EXAMPLES 15–16

Use is made of creatine kinase preparations of various animal species. The SH protection and fixing to dextran are carried out as in Example 13.

The finding again of the initial activities after storage of the control sera in liquid form for 3 weeks at 35° C. in an atmosphere of air is, for the individual enzymes, about 70%. The results obtained are summarised in the following Table 4:

TABLE 4

| source of the creatine kinase | activity yield (% of the initial activity) | % activity after storage for 3 weeks at 35° C. |
| --- | --- | --- |
| rabbit muscle | 65 | 71 |
| pig heart | 59 | 72 |
| bovine heart | 61 | 71 |

EXAMPLE 17

Native rabbit muscle creatine kinase, rabbit muscle creatine kinase with SH protection (reaction with cystine) unfixed and, in each case, fixed to water-soluble dextran T40 by means of TCT, BrCN and CDAP are, in each case, dissolved in 100 ml. fresh human serum. The creatine kinase activity is adjusted to 300 to 600 U/liter.

The preparation of the stable creatine kinase derivatives takes place according to Examples 1, 12, 13 or 14. There is used a protein:dextran ratio of 1:10 or 1:20.

All essential enzymes, substrates and metabolites are, if necessary, also added thereto so that a "universal" control or calibration serum is obtained.

The pH value of the control sera is adjusted to about 6.0 with 2N hydrochloric acid.

The solutions obtained are filtered clear, filled in 4 ml. portions into bottles and lyophilised. The lyophilised samples are stored at refrigerator temperature.

A part of the samples is kept for 3 weeks at 35° C. Thereafter, for testing the stability, there are determined the creatine kinase activities in the temperature stressed and unstressed samples after reconstitution with 4 ml. of water.

The pH value of the control/calibration sera, after reconstitution of the preparations with water, is about 7.0. The finding again of the creatine kinase activities in % in the stressed samples, compared with the unstressed samples, is set out in the following Table 5.

Some of the samples are, after reconstitution with water, to which is added for preserving 250 mg. sodium azide/liter and 100 mg. gentamycin/liter, stored for 3 weeks at 4° C. Each week, the creatine kinase activity is measured in the various samples and the finding again of the creatine kinase activity in the stored samples in % in comparison with the initial value is also given in the following Table 5.

TABLE 5

Stability of various creatine kinase (CK) derivatives in lyophilised or reconstituted control/calibration sera based on human serum (Example 17)

| | % activity | | | |
| --- | --- | --- | --- | --- |
| | in the lyophilisate after 3 weeks storage | after reconstitution and storage at 4° C. after | | |
| CK derivative | at 35° C. | 1 week | 2 weeks | 3 weeks |
| CK, native | 92 | 80 | 74 | 62 |

TABLE 5-continued

Stability of various creatine kinase (CK) derivatives in lyophilised or reconstituted control/calibration sera based on human serum (Example 17)

| CK derivative | % activity | | | |
|---|---|---|---|---|
| | in the lyophilisate after 3 weeks storage at 35° C. | after reconstitution and storage at 4° C. after | | |
| | | 1 week | 2 weeks | 3 weeks |
| CK + SH-protection | 92 | 86 | 81 | 69 |
| CK + SH-protection + fixed, TCT protein:dextran = 1:10 | 93 | 100 | 98 | 92 |
| CK + SH-protection + fixed, BrCN protein:dextran = 1:10 | 99 | 103 | 102 | 95 |
| CK − SH-protection + fixed, CDAP protein:dextran = 1:10 | 97 | 104 | 104 | 97 |
| CK + SH-protection + fixed, CDAP protein:dextran = 1:20 | 99 | 103 | 104 | 98 |

We claim:

1. A process for stabilizing a liquid form of creatine kinase by disulphide modification comprising reacting creatine kinase in liquid form in any desired sequence:
   (a) with a molar excess of disulphide and/or thiosulphonate and
   (b) with a molar excess of activated water-soluble carbohydrate as carrier so as to covalently bind said creatine kinase in liquid form to said carrier, wherein said enzyme and said activated water soluble carbohydrate are reacted in a weight ratio of enzyme to carbohydrate of from 1:2 to 1:30.

2. The process of claim 1, wherein the disulphide is one of cystine, homocystine, cystine methyl ester or cystamine.

3. The process of claim 2, wherein the thiosulphonate is methanethiosulphonic acid S-methyl ester.

4. The process of claim 3 wherein the creatine kinase is used in a concentration of 0.1 mmole/liter.

5. The process of claim 1 further comprising activating the carbohydrate with one of trichlorotriazine, cyanogen bromide or 1-cyano-4-dimethylaminopyridinium tetrafluoroborate.

6. The process of claim 1 wherein the ratio of creatine kinase to carbohydrate is from 1:10 to 1:30, by weight.

7. The process of claim 1 wherein the water soluble carbohydrate is dextran.

8. The process of claim 7, wherein the dextran has a molecular weight of from 4000 to 500,000.

9. The process of claim 1 wherein creatine kinase which has been isolated from rabbit muscle is reacted with cystine and subsequently reacted with dextran which has been activated with 1-cyano-4-dimethylaminopyridinium tetrafluoroborate, the ratio of protein to dextran being 1:20.

10. The process of claim 1 wherein the stabilised creatine kinase solution is covered with an inert protective gas.

11. The process of claim 10, wherein nitrogen is used as the inert protective gas.

12. A stabilized liquid form of creatine kinase, wherein the creatine kinase is present as a reaction product with a molar excess of a disulphide or thiosulphonate and is covalently bound to a water-soluble, activated carbohydrate, wherein said enzyme and said activated water soluble carbohydrate are in a weight ratio of from 1:2 to 1:30.

13. The process of claim 1 wherein wherein the thiosulphonate is methanethiosulphonic acid S-methyl ester.

14. The process of claim 1 wherein the creatine kinase is used in a concentration of 0.1 mmole/liter.

* * * * *